(12) United States Patent
Truckai et al.

(10) Patent No.: US 6,913,579 B2
(45) Date of Patent: Jul. 5, 2005

(54) ELECTROSURGICAL WORKING END AND METHOD FOR OBTAINING TISSUE SAMPLES FOR BIOPSY

(75) Inventors: Csaba Truckai, Saratoga, CA (US); Rodney Perkins, Woodside, CA (US); John H. Shadduck, Tiburon, CA (US)

(73) Assignee: SurgRx, Inc., Palo Alto, CA (US)

( * ) Notice: Subject to any disclaimer, the term of this patent is extended or adjusted under 35 U.S.C. 154(b) by 462 days.

(21) Appl. No.: 10/136,874

(22) Filed: Apr. 30, 2002

(65) Prior Publication Data

US 2002/0169392 A1 Nov. 14, 2002

Related U.S. Application Data

(60) Provisional application No. 60/288,152, filed on May 1, 2001.

(51) Int. Cl.$^7$ ............ A61B 10/00; A61B 18/18
(52) U.S. Cl. ............ 600/564; 606/39; 606/48
(58) Field of Search .............. 600/562, 564; 606/39, 41, 45, 48–50, 205, 208

(56) References Cited

U.S. PATENT DOCUMENTS

| | | |
|---|---|---|
| 659,409 A | 10/1900 | Mosher |
| 1,586,645 A | 6/1926 | Bierman |
| 1,798,902 A | 3/1931 | Raney |
| 1,881,250 A | 10/1932 | Tomlinson |
| 2,031,682 A | 2/1936 | Wappler et al. |
| 3,651,811 A | 3/1972 | Hildebrandt et al. |
| 3,685,518 A | 8/1972 | Beuerle et al. |
| 3,730,188 A | 5/1973 | Ellman |
| 3,768,482 A | 10/1973 | Shaw |
| 3,826,263 A | 7/1974 | Cage et al. |
| 4,092,986 A | 6/1978 | Schneiderman |
| 4,198,957 A | 4/1980 | Cage et al. |
| 4,200,111 A * | 4/1980 | Harris .................. 600/564 |
| 4,219,025 A | 8/1980 | Johnson |
| 4,231,371 A | 11/1980 | Lipp |
| 4,232,676 A | 11/1980 | Herczog |

(Continued)

FOREIGN PATENT DOCUMENTS

| | | |
|---|---|---|
| EP | 341 446 A2 | 4/1989 |
| EP | 517 244 B1 | 3/1996 |

(Continued)

OTHER PUBLICATIONS

Corson, S.L., "Two new laparoscopic instruments: Bipolar sterilizing forceps and uterine manipulator," *Medical Instrumentation*, 11(1):7–8 (1977).

(Continued)

*Primary Examiner*—Eric F. Winakur
(74) *Attorney, Agent, or Firm*—Townsend & Townsend & Crew LLP

(57) ABSTRACT

An electrosurgical working end and method for obtaining a tissue sample for biopsy purposes, for example, from a patient's lung or a liver. The working end provides curved jaw members that are positioned on opposing sides of the targeted anatomic structure. The working end carries a slidable extension member that is laterally flexible with inner surfaced that slide over the jaw members to clamp tissue therebetween. As the extension member advances, the jaws compress the tissue just ahead of the advancing extension member to allow the laterally-outward portion of the extension member to ramp over the tissue while a cutting element contemporaneously cuts the tissue. By this means, the transected tissue margin is captured under high compression. The working end carries a bi-polar electrode arrangement that engages the just-transected medial tissue layers as well as surface layers to provides Rf current flow for tissue welding purposes that is described as a medial-to-surface bi-polar approach.

20 Claims, 8 Drawing Sheets

U.S. PATENT DOCUMENTS

| | | |
|---|---|---|
| 4,271,838 A | 6/1981 | Lasner et al. |
| 4,353,371 A | 10/1982 | Cosman |
| 4,370,980 A | 2/1983 | Lottick |
| 4,375,218 A | 3/1983 | DiGeronimo |
| 4,492,231 A | 1/1985 | Auth |
| 4,590,934 A | 5/1986 | Malis et al. |
| 4,608,981 A | 9/1986 | Rothfuss et al. |
| 4,633,874 A | 1/1987 | Chow et al. |
| 4,655,216 A | 4/1987 | Tischer |
| 4,671,274 A | 6/1987 | Sorochenko |
| 4,691,703 A | 9/1987 | Auth et al. |
| 4,763,669 A | 8/1988 | Jaeger |
| 4,785,807 A | 11/1988 | Blanch |
| 4,848,337 A | 7/1989 | Shaw et al. |
| 4,850,353 A | 7/1989 | Stasz et al. |
| 4,887,612 A | 12/1989 | Esser et al. |
| 4,940,468 A | 7/1990 | Petillo |
| 4,958,539 A | 9/1990 | Stasz et al. |
| 4,969,885 A | 11/1990 | Farin |
| 4,985,030 A | 1/1991 | Melzer et al. |
| 5,009,656 A | 4/1991 | Reimels |
| 5,057,106 A | 10/1991 | Kasevich et al. |
| 5,057,107 A | 10/1991 | Parins et al. |
| 5,085,659 A | 2/1992 | Rydell |
| 5,104,025 A | 4/1992 | Main et al. |
| 5,122,137 A | 6/1992 | Lennox |
| 5,147,356 A | 9/1992 | Bhatta |
| 5,147,357 A | 9/1992 | Rose et al. |
| 5,151,102 A | 9/1992 | Kamiyama et al. |
| 5,190,541 A | 3/1993 | Abele et al. |
| 5,201,900 A | 4/1993 | Nardella |
| 5,207,691 A | 5/1993 | Nardella |
| 5,258,006 A | 11/1993 | Rydell et al. |
| 5,267,998 A | 12/1993 | Hagen |
| 5,269,780 A | 12/1993 | Roos |
| 5,269,782 A * | 12/1993 | Sutter .......................... 606/48 |
| 5,290,286 A | 3/1994 | Parins |
| 5,306,280 A | 4/1994 | Bregen et al. |
| 5,308,311 A | 5/1994 | Eggers et al. |
| 5,324,289 A | 6/1994 | Eggers |
| 5,336,221 A | 8/1994 | Anderson |
| 5,360,428 A | 11/1994 | Hutchinson, Jr. |
| 5,364,389 A | 11/1994 | Anderson |
| 5,389,098 A | 2/1995 | Tsuruta et al. |
| 5,403,312 A | 4/1995 | Yates et al. |
| 5,417,687 A | 5/1995 | Nardella et al. |
| 5,443,463 A | 8/1995 | Stern et al. |
| 5,445,638 A | 8/1995 | Rydell et al. |
| 5,451,224 A | 9/1995 | Goble et al. |
| 5,458,598 A | 10/1995 | Feinberg et al. |
| 5,480,397 A | 1/1996 | Eggers et al. |
| 5,480,398 A | 1/1996 | Eggers |
| 5,507,106 A | 4/1996 | Fox |
| 5,531,744 A | 7/1996 | Nardella et al. |
| 5,571,153 A | 11/1996 | Wallsten |
| 5,573,535 A | 11/1996 | Viklund |
| 5,593,406 A | 1/1997 | Eggers et al. |
| 5,611,798 A | 3/1997 | Eggers |
| 5,624,452 A | 4/1997 | Yates |
| 5,674,220 A | 10/1997 | Fox et al. |
| 5,693,051 A | 12/1997 | Schulze et al. |
| 5,716,366 A | 2/1998 | Yates |
| 5,735,848 A | 4/1998 | Yates et al. |
| 5,755,717 A | 5/1998 | Yates et al. |
| 5,766,166 A | 6/1998 | Hooven |
| 5,776,130 A | 7/1998 | Buysse et al. |
| 5,797,938 A | 8/1998 | Paraschal et al. |
| 5,797,957 A * | 8/1998 | Palmer et al. .............. 600/564 |
| 5,800,449 A | 9/1998 | Wales |
| 5,807,392 A | 9/1998 | Eggers |
| 5,833,690 A | 11/1998 | Yates et al. |
| 5,911,719 A | 6/1999 | Eggers |
| 5,947,984 A | 9/1999 | Whipple |
| 6,019,758 A | 2/2000 | Slater |
| 6,039,733 A | 3/2000 | Buysse et al. |
| 6,074,389 A | 6/2000 | Levine et al. |
| 6,086,586 A | 7/2000 | Hooven |
| 6,113,598 A | 9/2000 | Baker |
| 6,139,508 A | 10/2000 | Simpson et al. |
| 6,152,923 A | 11/2000 | Ryan |
| 6,162,220 A | 12/2000 | Nezhat |
| 6,174,309 B1 | 1/2001 | Wrublewski et al. |
| 6,176,857 B1 | 1/2001 | Ashley |
| 6,179,834 B1 | 1/2001 | Buysse et al. |
| 6,179,835 B1 | 1/2001 | Panescu et al. |
| 6,179,837 B1 | 1/2001 | Hooven |
| 6,187,003 B1 | 2/2001 | Buysse et al. |
| 6,190,386 B1 | 2/2001 | Rydell |
| 6,193,709 B1 | 2/2001 | Miyawaki et al. |
| 6,270,497 B1 | 8/2001 | Sekino et al. |
| 6,273,887 B1 | 8/2001 | Yamauchi et al. |
| 6,277,117 B1 | 8/2001 | Tetzlaff et al. |
| 6,296,640 B1 | 10/2001 | Wampler et al. |
| 6,328,703 B1 | 12/2001 | Murakami |
| 6,334,861 B1 | 1/2002 | Chandler et al. |
| 6,350,264 B1 | 2/2002 | Hooven |
| 6,352,536 B1 | 3/2002 | Buysse et al. |
| 6,398,779 B1 | 6/2002 | Buysse et al. |
| 6,409,725 B1 | 6/2002 | Khandkar et al. |
| 6,451,018 B1 | 9/2002 | Lands et al. |
| 6,458,128 B1 | 10/2002 | Schulze |
| 6,458,130 B1 | 10/2002 | Frazier et al. |
| 6,464,704 B2 | 10/2002 | Schmaltz |
| 6,468,275 B1 | 10/2002 | Wampler et al. |
| 6,500,176 B1 | 12/2002 | Truckai et al. |
| 6,511,480 B1 | 1/2003 | Tetzlaff et al. |
| 6,527,767 B2 | 3/2003 | Wang et al. |
| 6,533,784 B2 | 3/2003 | Truckai et al. |
| 6,554,829 B2 | 4/2003 | Schulze et al. |
| 6,575,968 B1 | 6/2003 | Eggers et al. |
| 6,585,735 B1 | 7/2003 | Frazier et al. |
| 6,632,193 B1 | 10/2003 | Davison et al. |
| 6,652,521 B2 | 11/2003 | Schulze |
| 2002/0052599 A1 | 5/2002 | Goble |
| 2002/0115997 A1 | 8/2002 | Truckai et al. |
| 2002/0120266 A1 | 8/2002 | Truckai et al. |
| 2002/0169392 A1 | 11/2002 | Truckai et al. |
| 2002/0177848 A1 | 11/2002 | Truckai et al. |
| 2003/0018327 A1 | 1/2003 | Truckai et al. |
| 2003/0050635 A1 | 3/2003 | Truckai et al. |
| 2003/0055417 A1 | 3/2003 | Truckai et al. |
| 2003/0069579 A1 | 4/2003 | Truckai et al. |
| 2003/0078573 A1 | 4/2003 | Truckai et al. |
| 2003/0078577 A1 | 4/2003 | Truckai et al. |
| 2003/0078578 A1 | 4/2003 | Truckai et al. |
| 2003/0114851 A1 | 6/2003 | Truckai et al. |
| 2003/0125727 A1 | 7/2003 | Truckai et al. |
| 2003/0139741 A1 | 7/2003 | Goble et al. |
| 2003/0144652 A1 | 7/2003 | Baker et al. |

FOREIGN PATENT DOCUMENTS

| | | |
|---|---|---|
| EP | 518 230 B1 | 5/1996 |
| FR | 2536924 A1 | 6/1984 |
| FR | 2647683 A1 | 12/1990 |
| GB | 2037167 A | 7/1980 |
| GB | 2066104 A | 7/1981 |
| GB | 2133290 A | 7/1984 |
| GB | 2160182 A | 1/1986 |
| SU | 342617 | 7/1972 |

| | | |
|---|---|---|
| SU | 575103 | 10/1977 |
| WO | WO 93/08754 A1 | 5/1993 |
| WO | WO 94/24949 A1 | 11/1994 |
| WO | WO 94/24951 A1 | 11/1994 |

OTHER PUBLICATIONS

Burton, J.D.K., "New Inventions," *The Lancet*, pp. 650–651 (1959).

Nardella, P.C., "Radio Frequency Energy and Impedance Feedback," *Proc. SPIE. Catheter–Based Sensing and Imaging Technology*, 1068: 42–48 (1989).

Vallfors et al., "Automatically controlled bipolar electrocoagulation—'COA–COMP'," *Neurosurg Rev.*, 187–190 (1984).

* cited by examiner

ELECTROSURGICAL WORKING END AND METHOD FOR OBTAINING TISSUE SAMPLES FOR BIOPSY

CROSS-REFERENCE TO RELATED APPLICATIONS

This application is related to the following U.S. patent applications: Ser. No. 09/694,233, filed Oct. 23, 2000, now U.S. Pat. No. 6,500,176 entitled Electrosurgical Systems and Techniques for Sealing Tissue; Provisional Patent Application Ser. No. 60/225,848, filed Dec. 14, 2000 entitled Electrosurgical Jaws for Controlled Application of Clamping Pressure; and Ser. No. 09/792,825, filed Feb. 24, 2001, now U.S. Pat. No. 6,533,784, entitled Electrosurgical Working End for Transecting and Sealing Tissue. All the above-listed patent applications are incorporated herein by this reference and this application claim benefit of 60/288,152 filed May 1, 2001.

FIELD OF THE INVENTION

This invention relates to medical devices and techniques and more particularly relates to the working end of an electrosurgical instrument that is adapted for the resection of tissue from a lung or liver for biopsy purposes while at the same time sealing the transected tissue margin.

BACKGROUND OF THE INVENTION

In various open and laparoscopic surgeries, it is necessary to seal or weld the margins of transected tissue volumes. However, satisfactory instruments have not been developed for electrosurgically excising a tissue biopsy sample from a lung or liver, for example, that seal the margin of the targeted structure while at the same time preventing gross thermal damage to resected tissue sample.

As background, various radiofrequency (Rf) surgical instruments have been developed for sealing the edges of transected tissues. For example, FIG. 1A shows a sectional view of paired electrode-jaws 2a and 2b of a typical prior art bi-polar Rf grasper grasping two tissue layers. In a typical bi-polar jaw arrangement, each jaw face comprises an electrode and Rf current flows across the tissue between the first and second polarities in the opposing jaws that engage opposing exterior surfaces of the tissue. FIG. 1A shows typical lines of bi-polar current flow between the jaws. Each jaw in FIG. 1A has a central slot adapted to receive a reciprocating blade member as is known in the art for transecting the captured vessel after it is sealed.

While bi-polar graspers as in FIG. 1A can adequately seal or weld tissue volumes that have a small cross-section, such bi-polar instruments are often ineffective in sealing or welding many types of anatomic structures, e.g., (i) anatomic structures having walls with irregular or thick fibrous content, such as lung tissue; (ii) bundles of disparate anatomic structures, and (iii) substantially thick anatomic and structures.

As depicted in FIG. 1A, a prior art grasper-type instrument is depicted with jaw-electrodes engaging opposing side of a tissue volume with substantially thick, dense and non-uniform fascia layers underlying its exterior surface. As depicted in FIG. 1A, the fascia layers f prevent a uniform flow of current from the first exterior tissue surface s to the second exterior tissue surface s that are in contact with electrodes 2a and 2b. The lack of uniform bi-polar current across the fascia layers f causes non-uniform thermal effects that typically result in localized tissue desiccation and charring indicated at c. Such tissue charring can elevate impedance levels in the captured tissue so that current flow across the tissue is terminated altogether. FIG. 1B depicts an exemplary result of attempting to create a weld across tissue with thick fascia layers f with a prior art bi-polar instrument. FIGS. 1A–1B show localized surface charring c and non-uniform weld regions w in the medial layers m of vessel. Further, FIG. 1B depicts a common undesirable characteristic of prior art welding wherein thermal effects propagate laterally from the targeted tissue causing unwanted collateral (thermal) damage indicated at d.

What is needed is an instrument working end that can utilize Rf energy (i) to transect tissue about a curved paths to recover tissue for biopsy purposes from a lung, liver or other anatomic structure; (ii) to substantially prevent thermal damage in the resected tissue sample; (iii) to provide a seal in tissue margin that limits collateral thermal damage; and (iv) to provide means for creating a seal or weld in substantially thick anatomic structures and tissue volumes that are not uniform in hydration, density and collagenous content.

SUMMARY OF THE INVENTION

The object of the present invention is to provide an instrument working end capable of transecting and compressing tissue to allow for controlled Rf energy delivery to transected tissue margins that have thick fascia layers or other tissue layers with non-uniform fibrous content. Such tissues are difficult to seal since the fascia layers can prevent uniform current flow and uniform ohmic heating of the tissue.

As background, the biological mechanisms underlying tissue fusion by means of thermal effects are not fully understood. In general, the delivery of Rf energy to a captured tissue volume elevates the tissue temperature and thereby at least partially denatures proteins in the tissue. The objective is to denature such proteins, including collagen, into a proteinaceous amalgam that intermixes and fuses together as the proteins renature. As the treated region heals over time, the biological weld is reabsorbed by the body's wound healing process.

In order to create an effective weld in a tissue volume dominated by the fascia layers, it has been found that several factors are critical. The objective is to create a substantially even temperature distribution across the targeted tissue volume to thereby create a uniform weld or seal. Fibrous tissue layers (i.e., fascia) conduct Rf current differently than adjacent less-fibrous layers, and it is believed that differences in extracellular fluid contents in such adjacent tissues contribute greatly to the differences in ohmic heating. It has been found that by applying high compressive forces to fascia layers and underlying non-fibrous layers, the extracellular fluids migrate from the site to collateral regions. Thus, the compressive forces can make resistance more uniform regionally within engaged tissue. Further, it has been found that that one critical factor in creating an effective weld across fibrous (fascia) layers is the delivery of bi-polar Rf energy from electrode surfaces engaging medial layers and surface (fascia) layers. In other words, effective current flow through the fascia layers is best accomplished by engaging electrodes on opposing sides of such fascia layers. Prior art jaw structures that only deliver bi-polar Rf energy from outside the surface or fascial layers cannot cause effective regional heating inward of such fascial layers (see FIGS. 1A–1B). For this reason, the novel technique causes Rf current flow to-and-from the medial (or just-transected) non-fascia layers at the interior of the structure, rather than to-and-from exterior surfaces only as in the prior art. This method is termed herein a medial-to-surface bi-polar delivery approach or a subfascia-to-fascia bi-polar approach.

Another aspect of the invention provides means for creating high compression forces a very elongate working end that engages the targeted tissue. This is accomplished by providing a slidable or translatable extension member that defines a receiving channel to engage the entire length of jaw members as the translatable member is extended over the jaws. The translatable member of the invention thus is adapted to perform several functions: (i) to contemporaneously transect the tissue and engage the transected tissue margins under high compression within components of the working end; and (ii) to provide spaced apart longitudinal electrode surfaces for delivery of Rf flow to each transected tissue margin from medial tissue layers to surface layers.

The combination of the translatable extension member in cooperation with the curved jaws members thus provides an electrode arrangement in engagement with the tissue margins that accomplishes the electrosurgical welding technique of the invention. Certain spaced apart portions of the translatable member carry electrode surfaces coupled to an Rf source. Thus, when the translatable extension member is moved to the extended position after transecting the engaged tissue volume, one medial electrode carried by the translatable member engages the medial or interior layers of the transected tissue margin. By this means, bi-polar current flows can be directed from the center portion of the extension member that engages medial or sub-fascial tissue layers to outward portions of the translatable member that engages opposing surface or fascial tissue layers of the tissue margin. It has been found that by engaging the medial portion of a just-transected structure with a first polarity electrode, and engaging the exterior surfaces of the structure with second polarity electrodes, a substantially uniform current flow through non-uniform fascia layers can be accomplished. This novel medial-to-surface bipolar approach of the invention also reduce or prevent tissue charring, and substantially prevents collateral thermal damage in the tissue by reducing stray Rf current flow through tissue lateral to the engaged tissue.

In another embodiment of the invention, the working end includes components of a sensor system which together with a power controller can control Rf energy delivery during a tissue welding procedure. For example, feedback circuitry for measuring temperatures at one or more temperature sensors in the working end may be provided. Another type of feedback circuitry may be provided for measuring the impedance of tissue engaged between various active electrodes carried by the working end. The power controller may continuously modulate and control Rf delivery in order to achieve (or maintain) a particular parameter such as a particular temperature in tissue, an average of temperatures measured among multiple sensors, a temperature profile (change in energy delivery over time), or a particular impedance level or range.

Additional objects and advantages of the invention will be apparent from the following description, the accompanying drawings and the appended claims.

BRIEF DESCRIPTION OF THE DRAWINGS

Other objects and advantages of the present invention will be understood by reference to the following detailed description of the invention when considered in combination with the accompanying Figures, in which like reference numerals are used to identify like components throughout this disclosure.

FIG. 4A depicting the positioning of the paired jaws over a targeted portion of a patient's lung;

FIG. 4B depicting the advancement of the translatable member over the jaw members to (i) transect the tissue to provide a biopsy sample and (ii) compressing the remaining tissue margin tightly between the jaw members for electrosurgical sealing; and FIG. 4C providing a sectional view taken along line 4C—4C of FIG. 4B to illustrate the path of Rf current flow through medial layers of the captured tissue.

DETAILED DESCRIPTION OF THE INVENTION

Figure 1A:
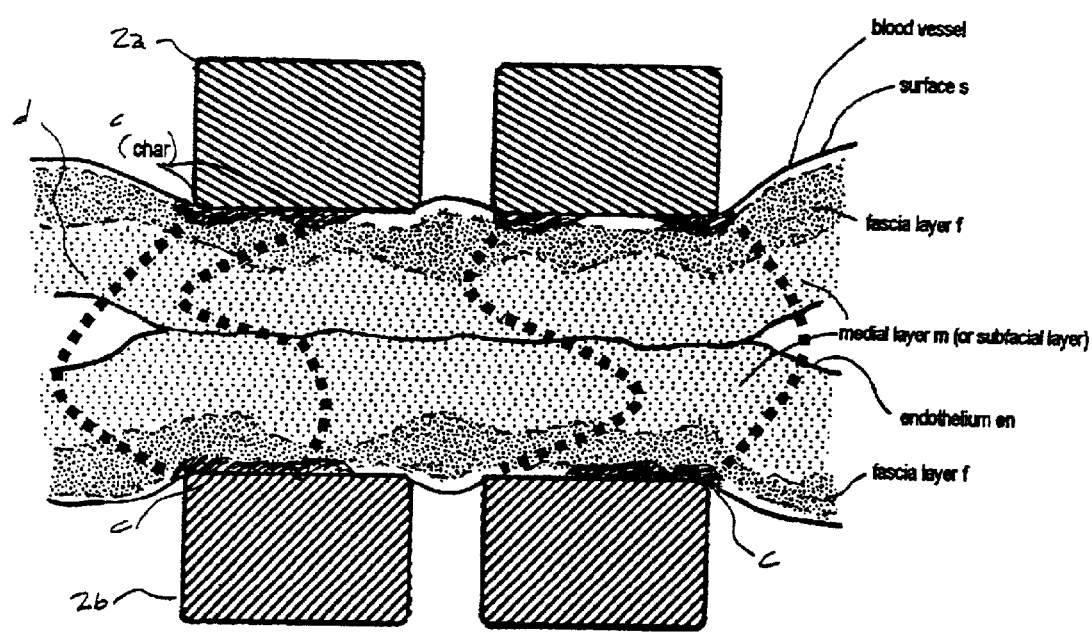
FIG. 1A is an illustration of current flow between the paired jaws of a prior art bi-polar radiofrequency device in a method of sealing a tissue with fascia layers that are resistant to Rf current flow therethrough.
Figure 1B:
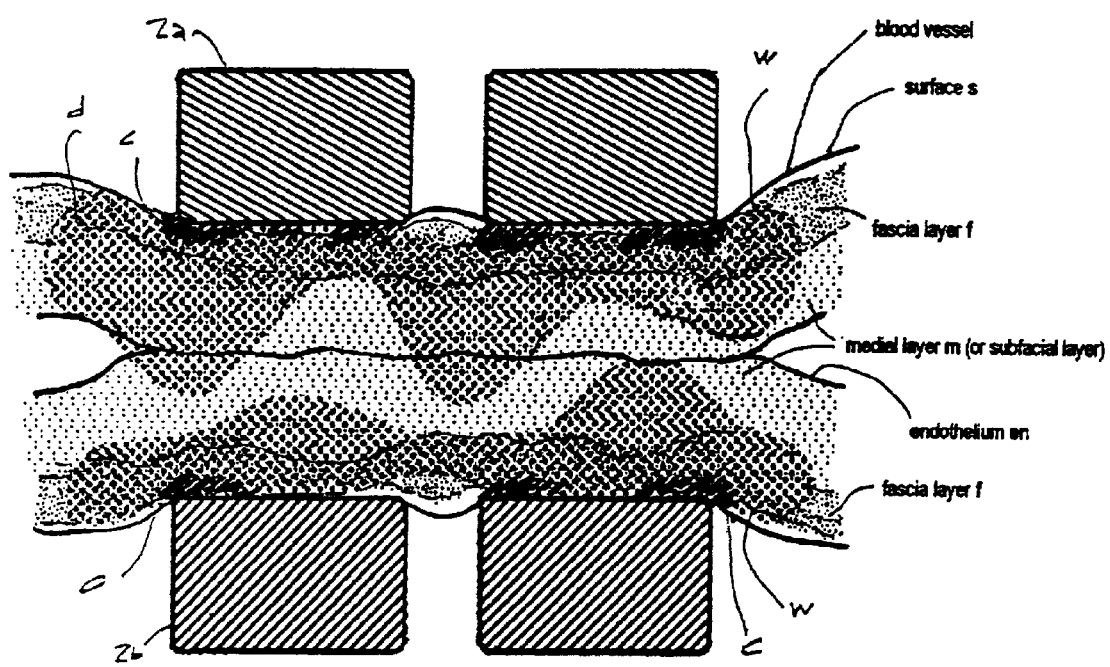
FIG. 1B illustrates representative weld effects of the bi-polar current flow of FIG. 1A.
Figure 2:
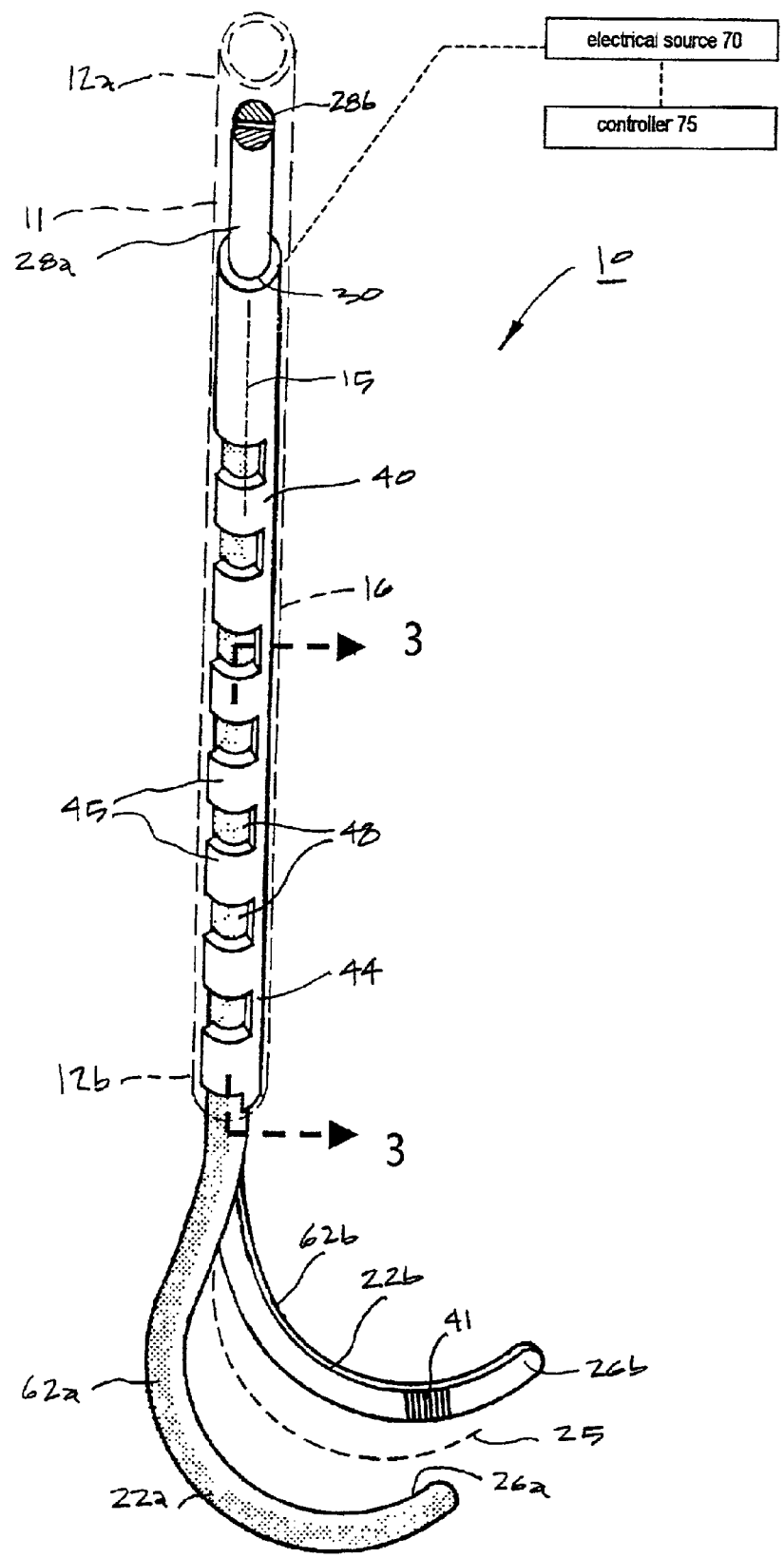
FIG. 2 is a view of an exemplary Type "A" working end corresponding to the present invention showing first and second jaw members extending from the distal end of an introducer body (phantom view), with a cooperating translatable extension member in a first non-extended position within the introducer body.

1. Type "A" Working End for Tissue Transection. Referring to FIG. 2, the working end 10 of an exemplary Type "A" embodiment is shown that is adapted for electrosurgically transecting a volume of tissue from a patient's lung or other targeted structure while at the same time sealing the transected tissue. The working end 10 comprises an introducer body portion 11 (phantom view) that extends from a proximal body end 12a to a distal body end 12b along longitudinal axis 15. In the exemplary embodiment of FIG. 2, the introducer body 10 can have a cylindrical or oval cross-section and comprise a thin-wall tubular sleeve 16 that extends from any suitable handle (not shown). The diameter of sleeve 16 can range from about 5 mm. to 10 mm., although other diameter instruments fall within the scope of the invention. The handle may be any type of pistol-grip or other type of handle known in the art that carries an actuator lever or slide to extend the translatable member 40 over first and second jaws 22a and 22b as will be described below.

Figure 3:
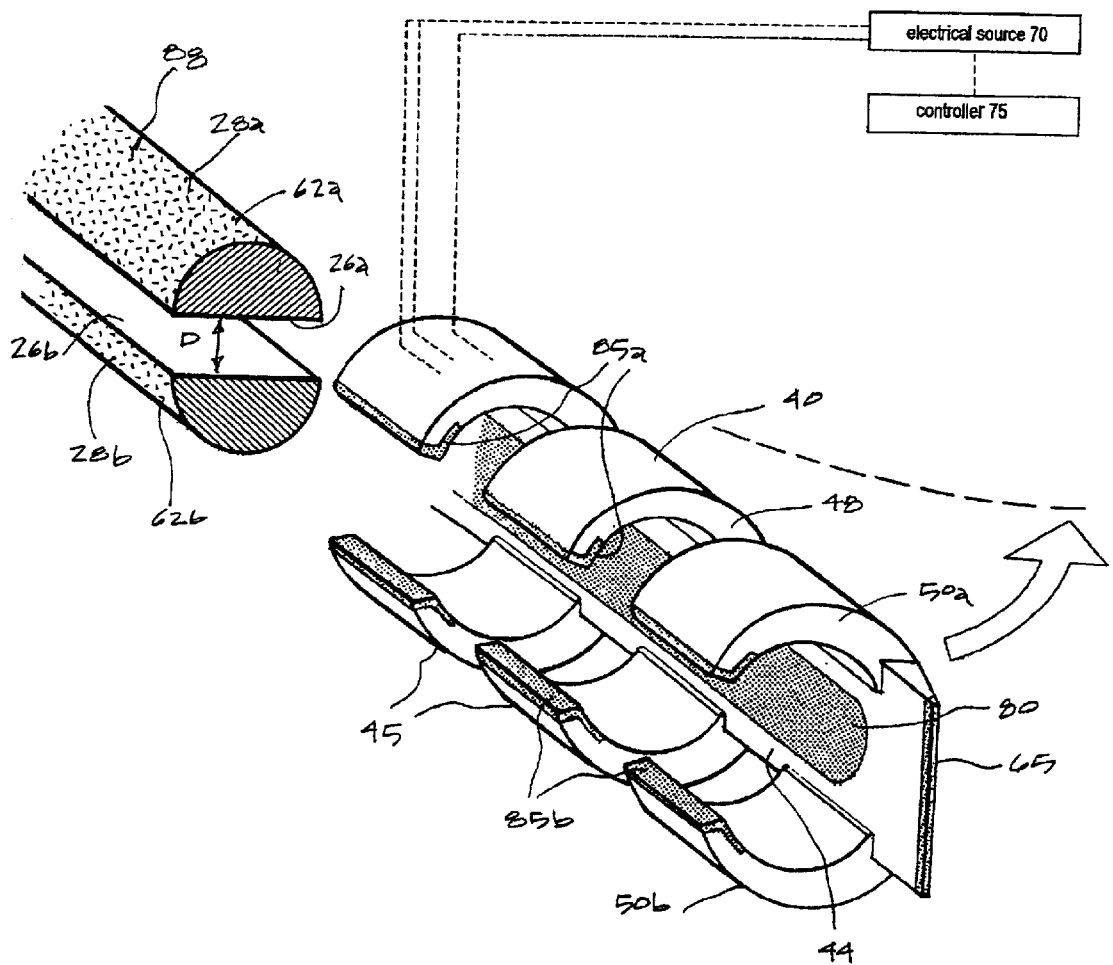
FIG. 3 is a perspective view of the proximal portions of the extending member that carry the paired jaws and a portion of the translatable member taken along line 3—3 of FIG. 2.

As can be seen in FIG. 2, the paired jaw member s 22a and 22b are formed to extend substantially rigidly about a curved axis indicated 25 that is defined by the jaw's cooperating engagements surfaces 26a and 26b in the closed position when engaging tissues. FIGS. 2–3 show that the independent jaw members 22a and 22b comprise the distal portion of elongate extension rod members 28a and 28b that extend from the instrument handle. The extension members 28a and 28b can have a cross-section ranging from about 0.05" to 0.20" and can have a flat surface so that the paired members can be slidably received by bore 30 in translatable member 40. The extension members and jaws 22a and 22b are formed of a suitable metal rod material with the flattened engagements surfaces 26a and 26b having serrations 41 another gripping surface for gripping tissue. It should be appreciated that curved portions of jaws 22a–22b can have any suitable radius or curve for transecting tissue of a selected dimension.

Of particular interest, FIGS. 3 & 4 illustrate the translatable member 40 that is adapted to perform multiple functions: (i) to provide a laterally-flexing cam mechanism that can slide over the curved jaws to thereby highly compress engagement surfaces 26a and 26b against opposing sides of the targeted tissue T; (ii) to contemporaneously transect the targeted tissue along a path p that is defined by the engagement axis 25 of the jaws, and (iii) in some embodiments, to carry electrode arrangements that can cooperate jaw electrodes to seal the margin of the transected tissue.

FIG. 3 shows a perspective view of translatable 40 and illustrates the manner in which the member is flexible to bend laterally to slide over the curved jaw members 22a and 22b (see FIG. 2) while at the same time providing cam surfaces for moving the jaws to the closed tissue-engaging position from the open position. In this exemplary embodiment, the translatable member 40 can be fabricated from a metal tubular material with sections removed therefrom or can be fabricated by plastic injection molding. No matter the material, the component comprise a laterally-flexing backbone portion indicated at 44 that is connected to jaw-engaging sections 45 (collectively) that are spaced apart along the backbone and separated by cuts or scallops 48 (collectively).

It can easily be seen how the translatable member 40 can bend laterally as depicted by the arrow in FIG. 3 to follow the curves of jaws 20a–20b. More in particular, this embodiment shows that jaw-engaging sections 45 comprise upper and lower "c"-shaped portions 50a and 50b that define inner surfaces 52a and 52b for slidably engaging the 22a and 22b about outward surfaces 62a and 62b thereof (FIG. 2). In this embodiment, the inner cam surfaces 52a–52b of translatable member 40 have a part-round cross-section to slidably cooperate with the rounded surfaces 62a–62b of the jaws, but it should be appreciated that any cooperating shapes are possible as long as the cam surfaces cam surfaces 52a–52b wrap partially (laterally) around the jaw members to insure that the "c"-shaped portions 50a–50b will track over the curved jaws as they compress the targeted tissue.

As can be seen in FIG. 3, the extension members and jaws 22a and 22b in the closed position define a dimension D between the engagement surfaces 26a and 26b which is selected as appropriate for engaging and compressing the targeted tissue, which is typically quite narrow and selected for the particular targeted tissue. In order to insure that the "c"-shaped portions 50a–50b of the translatable member 40 have sufficient strength to maintain their shape without flexing in order to compress the jaws over the targeted tissue, the cross-section of jaw-engaging sections 45 is made sufficiently thick or with any suitable reinforcing shown for additional strength.

Now turning to the electrosurgical functionality of the invention, FIG. 3 shows that distal termination 64 of the translatable member 40 carries an electrode cutting element indicated at 65. In the exemplary embodiment of FIG. 3, the translatable member 40 is of a molded non-conductive material and electrode 65 is coupled to electrical source 70 and controller 75 by electrical lead 76 that extends through backbone portion 44 of member 40. If the translatable member 40 is of a conductive metal, the distal cutting electrode 65 is insulated from the member as is known in the art, for example by providing an electrode carried over a thin insulated film backing.

Still referring to FIG. 3, it can be seen that translatable member 40 is further carries an electrode arrangement for sealing the tissue margin captured between the jaws 20a–20b. More in particular, member 40 has cooperating electrode surface portions 80 and 85a–85b that are exposed to contact the captured tissue: (i) at the transected medial tissue that interfaces the medial electrode 80, and (ii) at opposed exterior surfaces of the captured tissue that contacts the outboard electrodes 85a–85b, respectively (see FIG. 4C). For purposes of illustration, the exposed electrode surface portions 80 and 85a–85b are indicated in FIG. 3 to have a positive polarity (+) and negative polarity (–). These opposing polarity electrodes are, of course, spaced apart from one another and coupled to the electrical source 70 that defines the positive and negative polarities during operation of the instrument. The medial electrode 80 is coupled to electrical source 70 and controller 75 by lead 86 that extends through backbone portion 44 of the member. The outboard electrodes 85a–85b are similarly coupled to electrical source 70 and controller 75 by leads 87a and 87b. In the exemplary embodiment of FIG. 3, the extension members and jaw members 20a–20b have an insulative coating indicated at 88 so as to not provide a conductive path between the active electrodes.

Figure 4A:
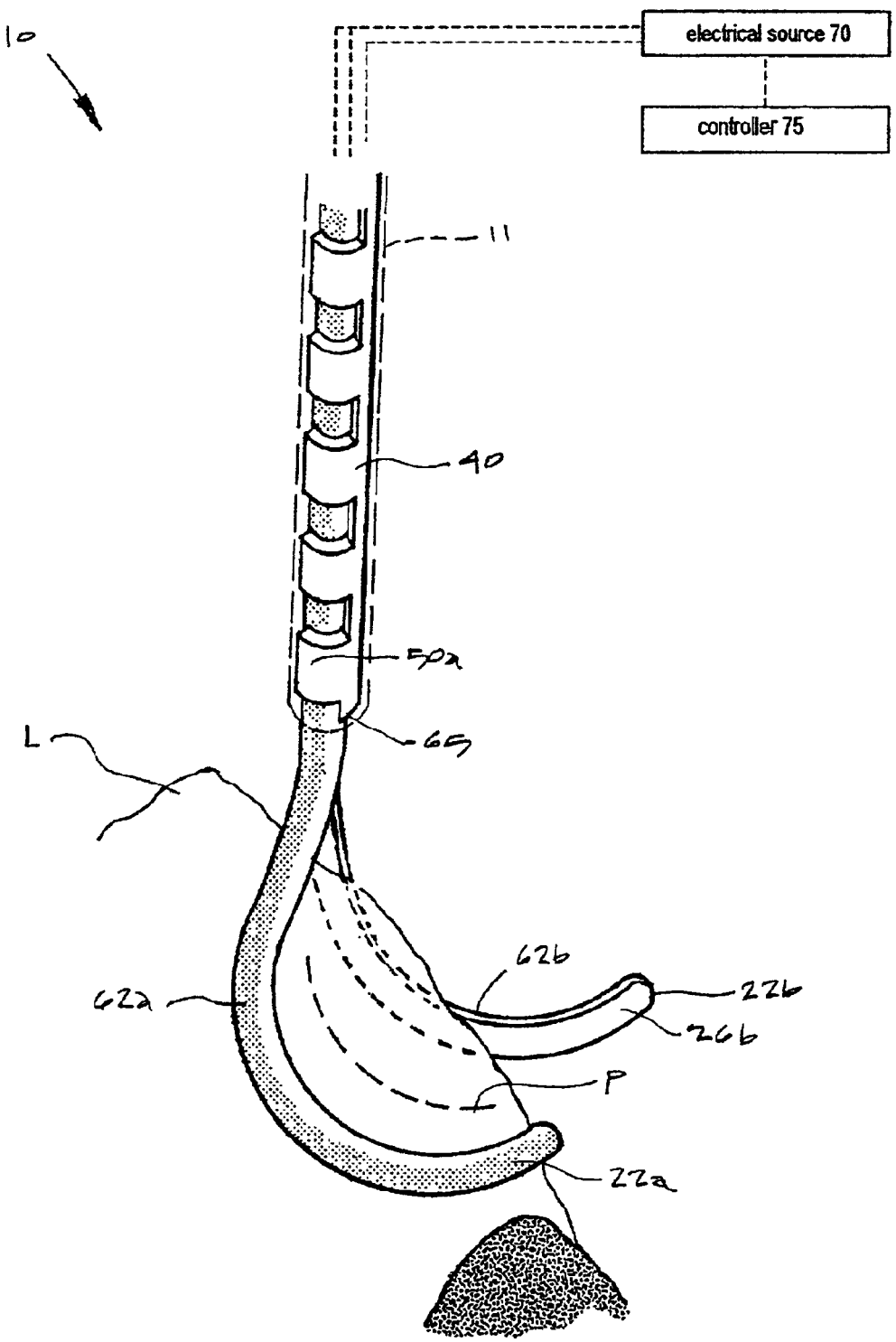
FIGS. 4A–4C are illustrations of the steps of practicing the method of the invention with the working end of FIG. 2.
Figure 4B:
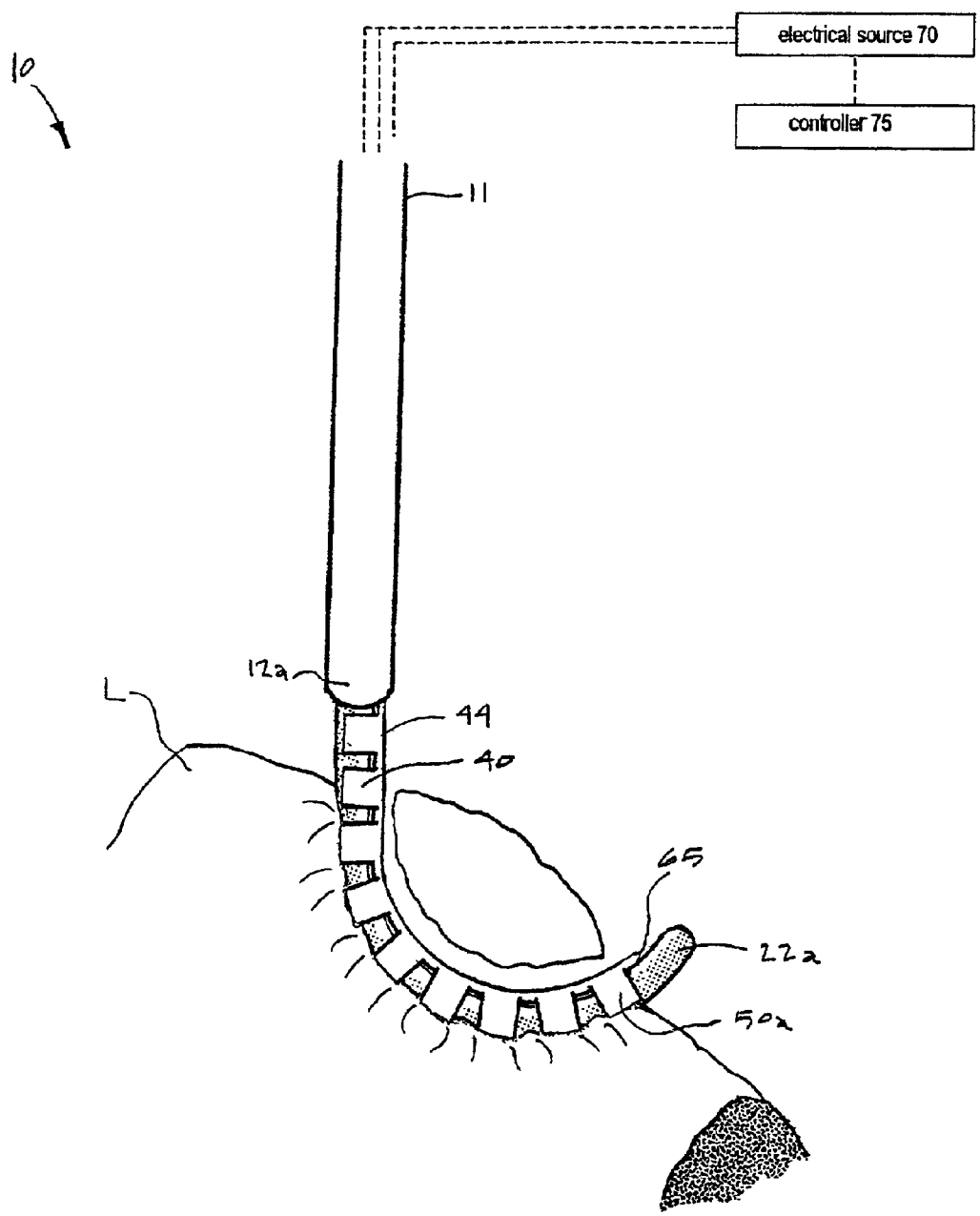

Now turning to FIGS. 4A–4C, the operation and use of the working end 10 of FIG. 2 in performing a method of the invention can be briefly described as follows. FIG. 4A depicts the working end being positioned over an edge of a patient's lung L (or other body structure) where the objective is to remove a tissue sample indicated at T. FIG. 4B shows the translatable member 40 being advanced from its non-extended (linear) position to its extended and curved distal position as it ramps over the tissue by advancing over the jaws members 20a–20b that compress the tissue just ahead of the advancing member 40. The laterally-outward portions of the translatable member 40 thereby slide over and engage the just-transected tissue margin m contemporaneous with cutting electrode 65 transecting the tissue. By this means, the tissue margins m is captured under high compression by the cooperating components of the working end 10. FIG. 4B also shows the tissue sample T being resected from the lung.

Figure 4C:
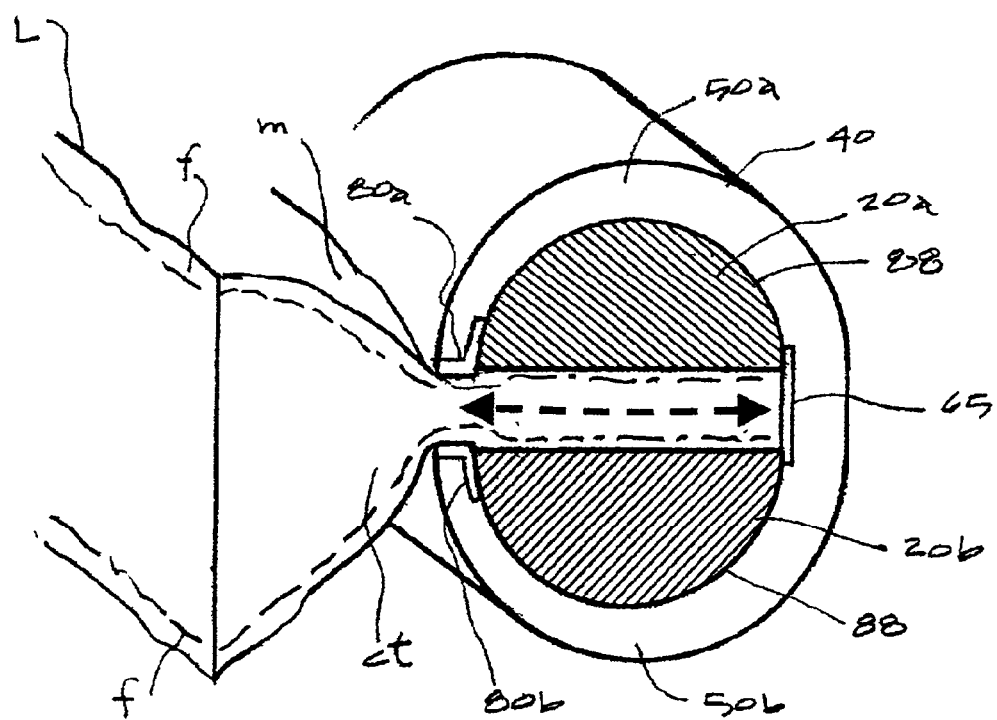

FIG. 4C depicts the tissue margins m captured between jaws members 20a–20b and upper and lower portions of the of jaw-engaging sections 45 of member 40. The tissue margin m may be any soft tissue or anatomic structure of a patient's body. In this example, the tissue is shown with a surface or fascia layer indicated at f and medial tissue layers mt. FIG. 4C provides an illustration of one preferred manner of Rf current flow that causes a sealing or welding effect by the medial-to-surface bi-polar current flow (or vice versa) indicated by arrows A. It has been found that a substantially uniform weld can be created across the captured tissue margin by causing current flow from exposed medial electrode surface 80 to electrodes 85a and 85b. In other words, the sectional illustration of FIG. 4C indicates that a weld can be created in the captured tissue margin where proteins (including collagen) are denatured, intermixed under high compressive forces, and fused upon cooling to seal or weld the transected tissue margin. Further, the desired weld effects can be accomplished substantially without collateral thermal damage to adjacent tissues indicated at ct in FIG. 4C.

Another embodiment of the invention (not shown) includes a sensor array of individual sensors (or a single sensor) carried in any part of the translatable member 40 or the jaws 20a–20a that contact engaged tissue. Such sensors preferably are located either under an electrode or adjacent to an electrode for the purpose of measuring temperatures of the electrode or tissue adjacent to an electrode during a welding procedure. The sensor array typically will consist of thermocouples or thermistors (temperature sensors that have resistances that vary with the temperature level). Thermocouples typically consist of paired dissimilar metals such as copper and constantan which form a T-type thermocouple as is known in the art. Such a sensor system can be linked to feedback circuitry that together with a power controller can control Rf energy delivery during a tissue welding procedure. The feedback circuitry can measure temperatures at one or more sensor locations, or sensors can measure the impedance of tissue, or voltage across the tissue, that is engaged between the electrodes carried by the working end. The power controller then can modulate Rf delivery in order to achieve (or maintain) a particular parameter such as a particular temperature in tissue, an average of temperatures measured among multiple sensors, a temperature profile (change in energy delivery over time), a particular impedance level or range, or a voltage level as is known in the art.

Figure 5:
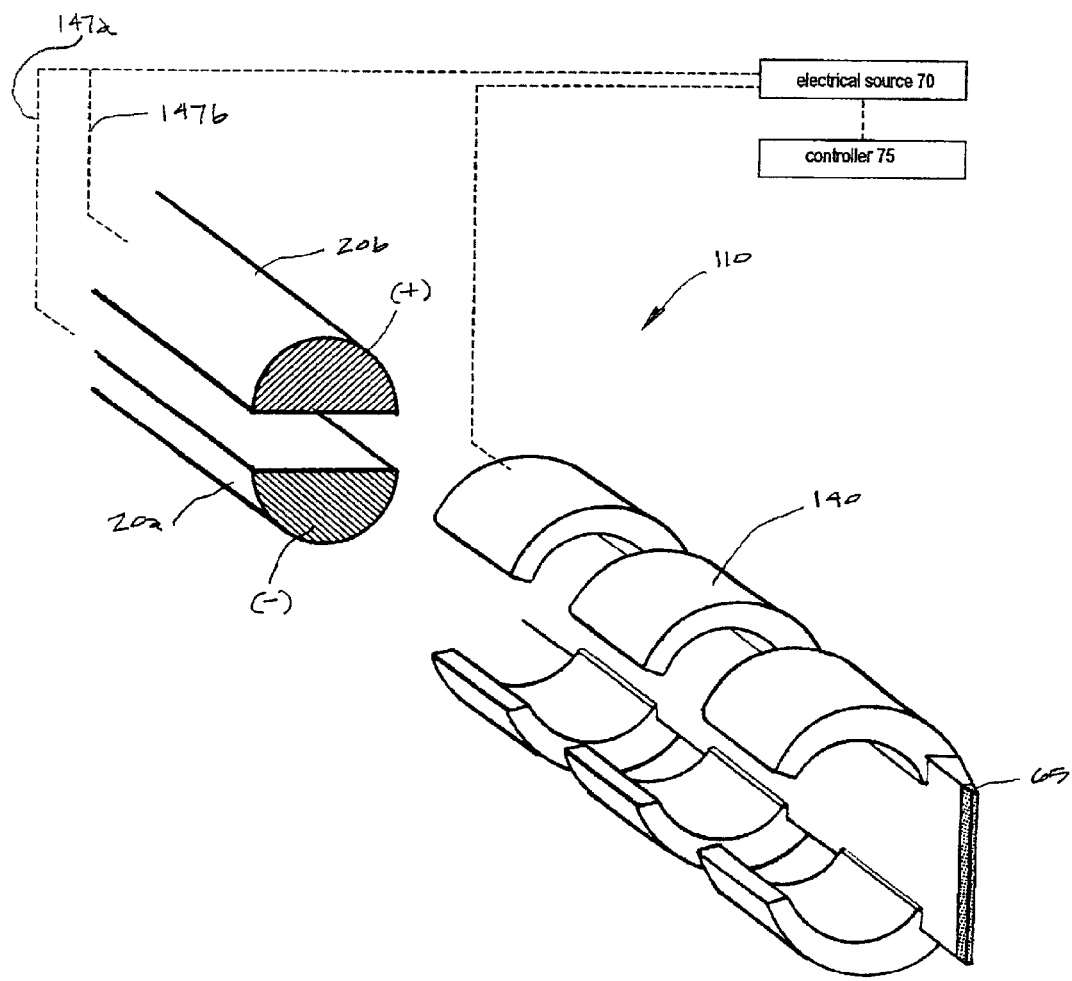
FIG. 5 is a view of a view of the components of a Type "B" working end wherein the jaws and translatable member provides a different electrode arrangement for sealing tissue.

2. Type "B" Working End for Tissue Transection. Referring to FIG. 5, components of a Type "B" working end 110 are shown that again are adapted for transecting and welding a tissue margin. This embodiment operates as described previously with translatable member 140 adapted to slide over the jaws 20a and 20b and again carries distal cutting electrode 65. However, in this embodiment, each jaw member 20a and 20b is coupled to electrical source 70 and controller 75 by electrical leads 147a and 147b to function as paired bi-polar electrodes with positive polarity (+) and negative polarity (−) indicated in FIG. 5. The paired jaw-electrodes themselves deliver Rf energy to the tissue which can be suitable for tissues that have substantially thin fascia layers and that have uniform collagenous content. In another embodiment (not shown) the translatable member can carry at least one electrode as depicted in FIG. 3 to cooperate with the active electrode jaws of FIG. 5. The controller 75 then can multiplex the Rf current flow along different selected paths among spaced apart electrodes as described in co-pending U.S. patent application Ser. No. 09/792,825 filed Feb. 24, 2001 titled *Electrosurgical Working End for Transecting and Sealing Tissue*, which is incorporated herein by reference. While FIGS. 2–5 depict an exemplary embodiment that uses a high-voltage cutting electrode to transect tissue, it should be appreciated that the cutting element also can be a sharp blade member.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. An electrosurgical instrument, comprising:
   an instrument body extending along a linear axis between a handle end and a distal body end;
   a pair of curved jaw members coupled to said distal body end that close about a curved tissue-engaging axis;
   a laterally-flexing translatable member in a first non-extended position is slidably carried by said linear instrument body and in a second extended position slidably coupled to said curved jaw members to thereby move said jaws from an open position to a closed position about said tissue-engaging axis; and
   a tissue-cutting element carried at a distal end of said translatable member for cutting tissue proximate to said tissue-engaging axis.

2. The working end of claim 1 wherein said tissue-cutting e element comprises a cutting electrode coupled to an electrical source.

3. The working end of claim 1 wherein the translatable member
   defines inner surfaces that slidably engage outer surfaces of said jaws.

4. The working end of claim 3 wherein the translatable member defines a first side comprising a flexible backbone portion and a second side defining a longitudinal opening for slidably receiving a transected tissue margin.

5. The working end of claim 4 wherein said inner surface of the translatable member carries spaced apart first and second polarity electrodes.

6. The working end of claim 5 wherein said first polarity electrode comprises elongate element exposed at said inner surface along said backbone portion.

7. The working end of claim 5 wherein said second polarity electrode comprises exposed elements proximate to said longitudinal opening.

8. The working end of claim 1 wherein said tissue-cutting element is selected from the group consisting of cutting electrodes and cutting blades.

9. A method of using an electrosurgical working end to obtain a tissue sample and seal the tissue margin, comprising:
   (a) capturing tissue between first and second curved jaw members carried by an electrosurgical working end;
   (b) advancing a laterally-flexible extension member over the first and second jaw members wherein inner surfaces of the extension member slidably engage outer surfaces of said first and second jaw members for closing the jaws over the tissue;
   (c) wherein a cutting element carried at the distal end of said extension member transects the tissue contemporaneous with closing the first and second jaws; and
   (d) delivering Rf current to the tissue captured between the first and second jaws from at least one electrode surface carried by the working end.

10. The method of claim 9, wherein the step (d) delivers Rf current between a first polarity electrode engaging medial layers of the transected tissue margin and a second polarity electrode engaging surface layers of the engaged tissue.

11. The method of claim 9, wherein step (d) delivers Rf current between first and second polarity electrodes engaging opposing surface layers of the captured tissue.

12. The method of claim 9, wherein step (d) delivers Rf current in a multiplexed manner between first and second polarity electrodes engaging medial and surface layers, respectively, and between first and second polarity electrodes engaging opposing surface layers of the transected tissue margin.

13. The method of claim 9, wherein step (c) utilizes a cutting electrode to transect tissue.

14. The method of claim 9, wherein step (c) utilizes a cutting blade to transect tissue.

15. The method of claim 9, wherein the tissue is in a patient's lung.

16. The method of claim 9, wherein the tissue is in a patient's liver.

17. A working end of an electrosurgical instrument for transecting and sealing tissue, comprising:

first and second curved jaws coupled to a distal end of an introducer member;

an extension member defining first and second inner longitudinal surfaces for slidably engaging first and second outer surfaces of said first and second jaws, said extension member further defining a longitudinal opening for receiving tissue;

a cutting element carried about a distal terminus of the extension member; and at least one exposed electrode extending along a substantial length of the working end.

18. The working end of claim 17 said inner longitudinal surfaces define a laterally outward surface portion and a laterally inward surface portion, and each laterally inward and outward surface portion carrying an electrode.

19. The working end of claim 17 wherein said at least one exposed electrode comprises opposing polarity electrodes extending along engagement surfaces of said first and second curved jaws.

20. The working end of claim 17 wherein the jaws comprise an electrically conductive material.

* * * * *